US007811243B1

(12) United States Patent
Kollmann

(10) Patent No.: US 7,811,243 B1
(45) Date of Patent: Oct. 12, 2010

(54) REVERSE APPLIED PINPOINT PRESSURE SYSTEM AND METHOD OF USE

(76) Inventor: Ronald J. Kollmann, 238 Davis Rd., Hardyston, NJ (US) 07416

( * ) Notice: Subject to any disclaimer, the term of this patent is extended or adjusted under 35 U.S.C. 154(b) by 818 days.

(21) Appl. No.: 11/708,527

(22) Filed: Feb. 21, 2007

(51) Int. Cl.
*A47G 9/00* (2006.01)
*B68C 5/00* (2006.01)
*A61F 5/00* (2006.01)

(52) U.S. Cl. .............................. 602/19; 602/5; 54/79.1; 5/482; 5/485; 5/486

(58) Field of Classification Search ..................... 602/5, 602/19, 60; 54/79.1; D6/603; 428/98, 172, 428/173, 909; 5/482, 485, 486
See application file for complete search history.

(56) References Cited

U.S. PATENT DOCUMENTS

| | | | | | |
|---|---|---|---|---|---|
| 530,864 | A | * | 12/1894 | Torrey | 54/66 |
| 2,248,768 | A | * | 7/1941 | Licht | 5/485 |
| 2,720,269 | A | * | 10/1955 | Diacos | 169/50 |
| 3,801,416 | A | * | 4/1974 | Gulbierz | 109/49.5 |
| 3,924,851 | A | * | 12/1975 | Winston | 482/105 |
| 4,650,002 | A | * | 3/1987 | Pierce, Jr. | 169/50 |
| 4,709,430 | A | * | 12/1987 | Nicoll | 5/417 |
| 4,839,934 | A | * | 6/1989 | Rojas | 5/502 |
| 4,956,218 | A | * | 9/1990 | Haining | 428/102 |
| 5,076,575 | A | * | 12/1991 | Eylander | 482/105 |
| 5,083,617 | A | * | 1/1992 | Pierce, Jr. | 169/50 |
| 5,187,825 | A | * | 2/1993 | Tesch | 5/502 |
| 5,199,121 | A | * | 4/1993 | Payne | 5/502 |
| 5,211,163 | A | * | 5/1993 | Mortenson | 600/594 |
| 5,490,567 | A | * | 2/1996 | Speer | 169/50 |
| 5,547,445 | A | * | 8/1996 | Chang | 482/105 |
| 5,937,441 | A | * | 8/1999 | Raines | 2/69 |
| 6,243,896 | B1 | * | 6/2001 | Osuna et al. | 5/502 |
| 6,557,176 | B2 | * | 5/2003 | Franco-Sion | 2/102 |
| 6,634,160 | B1 | * | 10/2003 | Brauckmann-Towns | 54/71 |
| 6,692,413 | B1 | * | 2/2004 | Greenberg et al. | 482/105 |
| 6,757,916 | B2 | * | 7/2004 | Mah et al. | 2/456 |
| 6,961,970 | B2 | * | 11/2005 | Pedersen | 5/502 |
| 7,162,756 | B2 | * | 1/2007 | Schweigert | 5/502 |
| 7,376,979 | B2 | * | 5/2008 | Nilsen | 2/69 |
| 7,406,728 | B2 | * | 8/2008 | VanNeste | 5/486 |
| 2006/0024471 | A1 | * | 2/2006 | Cunningham | 428/81 |
| 2006/0174410 | A1 | * | 8/2006 | Mastandrea, Jr. | 5/482 |
| 2007/0113339 | A1 | * | 5/2007 | Field et al. | 5/482 |

* cited by examiner

*Primary Examiner*—Patricia M Bianco
*Assistant Examiner*—Brandon Jackson
(74) *Attorney, Agent, or Firm*—LaMorte & Associates

(57) ABSTRACT

A system and method for applying therapeutic forces to the vertebrae contained within a section of a patient's spine. The system utilizes a flexible pressure blanket having two ends and both a top surface and a bottom surface that extend between those two ends. A patient is asked to lie in a supine position on an elevated platform. The flexible pressure blanket is draped over the patient, wherein a central section of the flexible pressure blanket contacts the patient and end sections dangle freely on opposite sides of said patient. Weight elements are attached to the flexible pressure blanket to effect therapeutic forces upon the spine of the patient. The weight elements can be attached in-line with individual vertebrae in the spine. In this manner, forces acting in different directions can be experienced by the spine, thereby manipulating the spine from the benefit of the patient.

15 Claims, 4 Drawing Sheets

REVERSE APPLIED PINPOINT PRESSURE SYSTEM AND METHOD OF USE

BACKGROUND OF THE INVENTION

1. Field of the Invention

The present invention relates to weighted devices, that are placed on the body to affect the curvature of the spine. More particularly, the present invention relates to weighted devices that are intended to affect the lordotic curvature of the spine.

2. Prior Art Description

Many people suffer from back pain that is caused by the misalignment or compression of the vertebrae within the spine. When viewed from the back, a person's spine should be straight. When viewed from the side. A person's spine should have a normal lordotic curvature. The shape of the spine is governed by the condition of the discs that are interposed between the vertebrae and the conditions of the muscles that pull upon the spine.

When a back muscle is strained or when a disc becomes overly compressed, back pain can occur. Back pain of this nature is experienced by millions of people each year. In mild cases, people ignore the back pain until the body heals itself. If the back pain is more severe, a person may take a pain reliever to mask the pain until the body can heal itself. In cases of severe back pain or persistent back pain, a person may take stronger pharmaceuticals and may turn to a healthcare professional for treatment. For back pain, the healthcare professional most often consulted is a chiropractor.

Chiropractors treat back pain in many ways. One of the most common and effective ways used is to physically manipulate the spine. If a chiropractor can identify where a disc is compressed, the compression can often be relieved through physical manipulation of the spine. Similarly, if a muscle pull has caused stress upon the spine, that stress can also often be relieved through the physical manipulation of the spine.

Properly manipulating the spine to relieve pain requires significant skill. Some chiropractors are better than others. Many variables affect the ability of a chiropractor to manipulate a person's spine. These variables include, but are not limited to, the size of the patient, the degree of spine correction needed, the time available for treatment, and both the strength and competence of the chiropractor. In a typical visit to a chiropractor's office, the chiropractor often has less than a half hour to work with a single patient. If that time is insufficient to alleviate the patient's back pain, then the patient must schedule another appointment.

A need therefore exists for a system and method of manipulating the spine that can be used by a healthcare provider that can be precisely controlled, yet does not require the healthcare provider's constant attention or rely on the healthcare provider's physical skill. In this manner, corrective manipulations to the spine can be performed on a patient without the healthcare provider needing to be constantly present. A patient can therefore be tended to by the staff of the healthcare provider, thereby enabling a patient to receive longer, more effective and less expensive treatments. This need is met by the present invention as described and claimed below.

SUMMARY OF THE INVENTION

The present invention is a system and method for applying therapeutic forces to the vertebrae contained within a section of a patient's spine. The system utilizes a flexible pressure blanket having two ends and both a top surface and a bottom surface that extend between those two ends.

A patient is asked to lie in a supine position on an elevated platform. The flexible pressure blanket is draped over the patient, wherein a central section of the flexible pressure blanket contacts the patient and end sections dangle freely on opposite sides of said patient. Weight elements are attached to the flexible pressure blanket to effect therapeutic forces upon the spine of the patient. The weight elements can be attached in-line with individual vertebrae in the spine. In this manner, forces acting in different directions can be experienced by the spine, thereby manipulating the spine from the benefit of the patient.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention system can be used to apply a directed force to many parts of the anatomy within the torso, such as applying pressure to a kidney, the present invention system is especially effective when used to manipulate the spine. Accordingly, the exemplary embodiment of the present invention system that is illustrated shows its use in aligning the spine, therein presenting the best mode contemplated for the invention. However, the exemplary embodiment should not be considered a limitation on the present invention system as it is defined by the appended claims.

Figure 1:
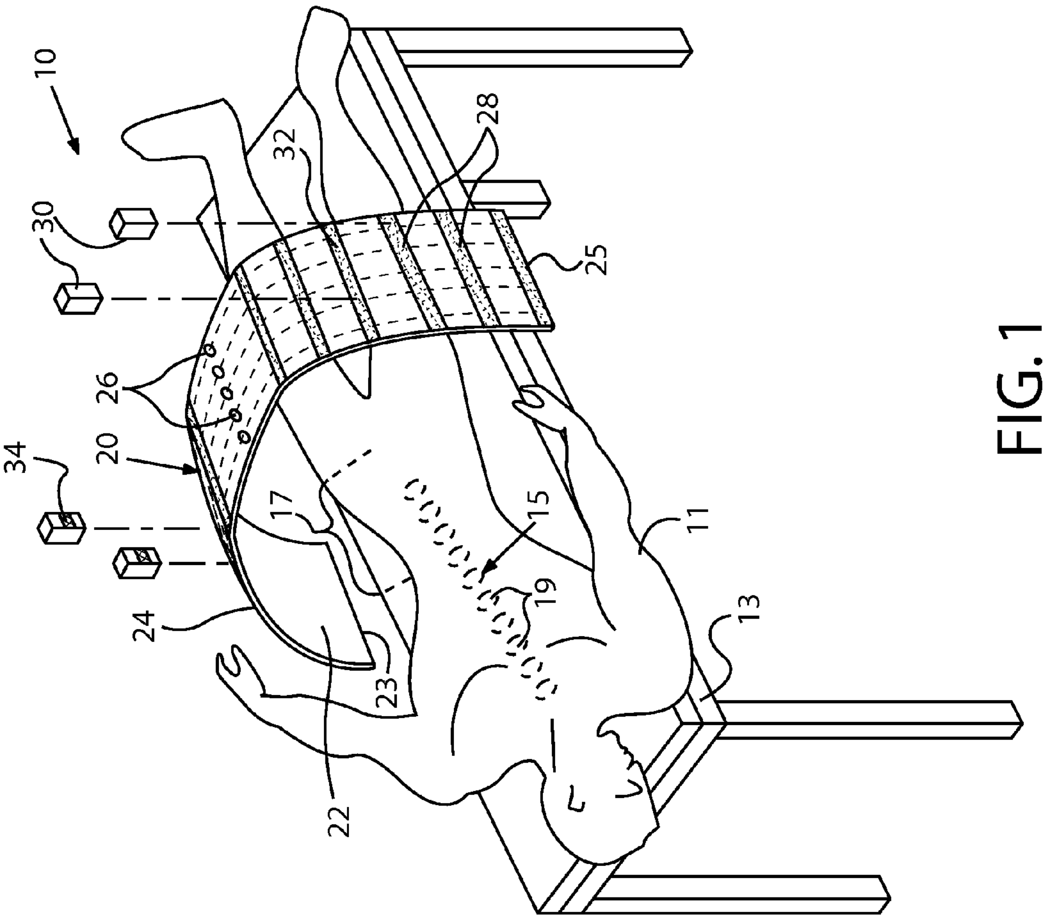
FIG. 1 is an exploded, perspective view of an exemplary embodiment of the present invention shown in conjunction with a patient and a table.

Referring to FIG. 1, there is shown an exemplary embodiment of the present invention system 10 shown in conjunction with a patient 11 lying in a supine position on a table 13. The purpose of the system 10 is to apply directed forces to the patient's spine 15, especially in the lower lumbar region 17, that can be used to physically manipulate the spine 15 for therapeutic purposes.

The present invention system 10 contains a pressure blanket 20. The pressure blanket 20 is flexible and can be made from a variety of materials. Although material such as plastic and leather can be used, it is preferred that the pressure blanket 20 be made of woven synthetic or natural fibers, so that it can be periodically laundered in a washing machine or otherwise treated with antiseptic spray.

The pressure blanket 20 has a width between eight inches and twenty-four inches. A preferred width is approximately fourteen inches. With the preferred width, the pressure blanket 20 will be at least as wide as the lower lumber region 17 of most patients.

The pressure blanket 20 also has a length between thirty-six and eighty inches. A preferred length is approximately sixty-six inches long. With the preferred length, the pressure blanket 20 will pass over the girth of a large patient, while still having ends that hang freely below the side of the patient.

The pressure blanket 20 presents an interior surface 22 and an exterior surface 24 that extend between two opposing ends 23, 25. The interior surface 22 rests against the patient 11. The interior surface 22 of the pressure blanket 20 may be slightly padded or may be lined thin line to absorb body moisture.

When a patient 11 is lying upon his/her back, the spine 15 cannot be directly observed. However, using various observable anatomical features, such as the position of the patient's ribs, the location of vertebrae 19 in the spine 15 can be estimated. Depending upon the width selected for the pressure blanket 20, the pressure blanket 20 will be as wide as a series of vertebrae 19 contained in the spine 15. The series of vertebrae 19 may contain between two and ten vertebrae, depending upon the size of the pressure blanket 20 and the size of the patient.

Indicia 26 are provided in the center of the pressure blanket 20 on its exterior surface 24. The indicia 26 can be markings or even holes formed through the pressure blanket 20. The indicia 26 are aligned in a straight row and are spaced similar to the average vertebrae spacing for an adult. In this manner, when the pressure blanket 20 is laid across the belly or chest of a patient 11 who is in a supine position, a good visual indication is present as to the positions of the underlying vertebrae 19 in the spine 15.

The exterior surface 24 of the pressure blanket 20 contains a plurality of attachment points 28 for weight elements 30. In the shown embodiment, the attachment points 28 are strips of hook and loop material 32. The hook and loop material 32 is laid out in parallel bands that extend across the width of the pressure blanket 20. The weight elements 30 are preferably weight-filled bags that also contain sections of hook and loop material 34. In this manner, it will be understood that any of the weight elements 30 can be attached to any of the attachment points 28 on the pressure blanket 20. It will, therefore, be understood that individual weight elements 30 can be attached to the pressure blanket 20 at different points along its length. Furthermore, weight elements 30 can be attached in line with the various indicia 26 in the center of the pressure blanket 20. This enables different weight elements 30 to be attached directly in line with different vertebrae 19 of the spine 15.

The weight elements 30 may all have the same mass or may vary in weight. It is preferred that the weight elements 30 be flexible, such as bags filled with ball bearings, rather than solid hunks of steel. By providing a flexible weight element 30, it is less likely that a weight element will cause discomfort to a patient should it come to rest directly upon the patient.

It will be understood that the use of hook and loop material to connect the weight elements 30 to the pressure blanket 20 is merely exemplary. Many other attachment means can be used and are intended to be included within the scope of this disclosure. Such attachment means include, but are not limited to, clips, ties, hooks and the use of pockets in the pressure blanket 20. What is of importance is that the weights elements 30 have the ability to be attached to different areas of the pressure blanket 20 and in varying numbers.

Figure 2:
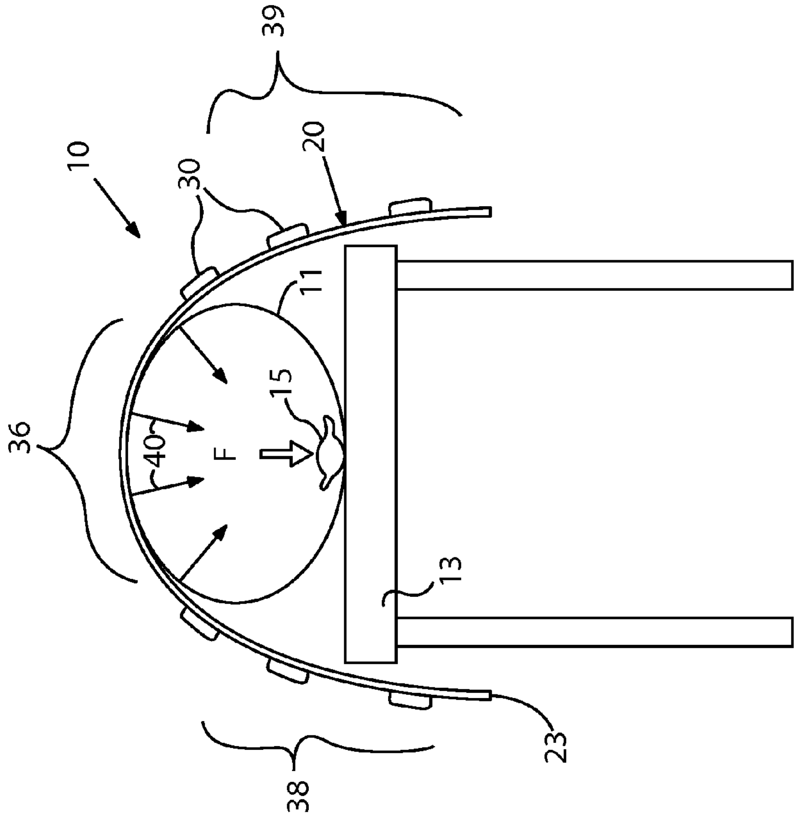
FIG. 2 is a cross-sectional view showing how forces from the present invention affect the spine within a patient's body.

Referring to FIG. 2 in conjunction with FIG. 1, it can be seen that to utilize the present invention system 10, a patient 11 is asked to lie upon a table 13 or narrow bed. Depending upon the diagnosis by the healthcare professional and the type of spine manipulation being attempted, the patient 11 may be instructed to lay either face-up or face down. In both FIG. 1 and FIG. 2, the'patient 11 is shown lying in a face-up, or supine, position.

The pressure blanket 20 is placed over the body of the patient 11 above the area of the spine 15 that is to be influenced. The pressure blanket 20 extends over the body and hangs freely off the sides of the table 13, below the sides of the patient 11. Accordingly the pressure blanket 20 rests in an inverted U-shape, having a curved section 36 it contacts the patient's body and straight sections 38, 39 near the free ends 23, 25 that are hanging freely.

When the human body is laying flat upon its back, the torso of the body presents a generally oval-shaped cross-sectional profile. As is indicated in FIG. 2, the spine 15 is located in the bottom-center of that cross-sectional profile. The weight elements 30 are selectively added to the exterior surface 24 of the pressure blanket 20. If the weight elements 30 are symmetrically added to the hanging straight sections 38, 39 of the pressure blanket 20, the downward forces of the weight elements 30 are resisted by the patient's body. The combined weight of the weight elements 30 is distributed across the curved section 36 of the pressure blanket 30 that contacts the patient's body. Due to the natural curvature of the patient's body, the combined weight of the weight elements 30 presses inwardly upon the patient's body as is indicated by force arrows 40. All of the force arrows 40 generally point toward the spine 15 of the patient 11. It will therefore be understood that the one area of the body that receives the most concentrated forces is the spine 15. The result is a cumulative downward force F on the spine 11 only under the area of the pressure blanket 20.

In addition to directing forces toward the spine 15, the pressure blanket 20 also presses inwardly on the torso of the patient's body. This helps prevents the tissue and organs of the patient 11 from spreading under the pressure blanket 20 as the patient 11 lies upon the table 13. The result is that more of the patient's own weight is concentrated upon the spine 11.

From FIG. 2, it will be understood that by symmetrically applying weight elements 30 to the pressure blanket 20 on either side of a patient's body, an even downward force can be applied to the narrow section of the spine 11 that lies under the pressure blanket 20. The degree of the downward force can be selectively controlled by regulating the number of weight elements 30 attached to either side of the patient's body.

Figure 3:
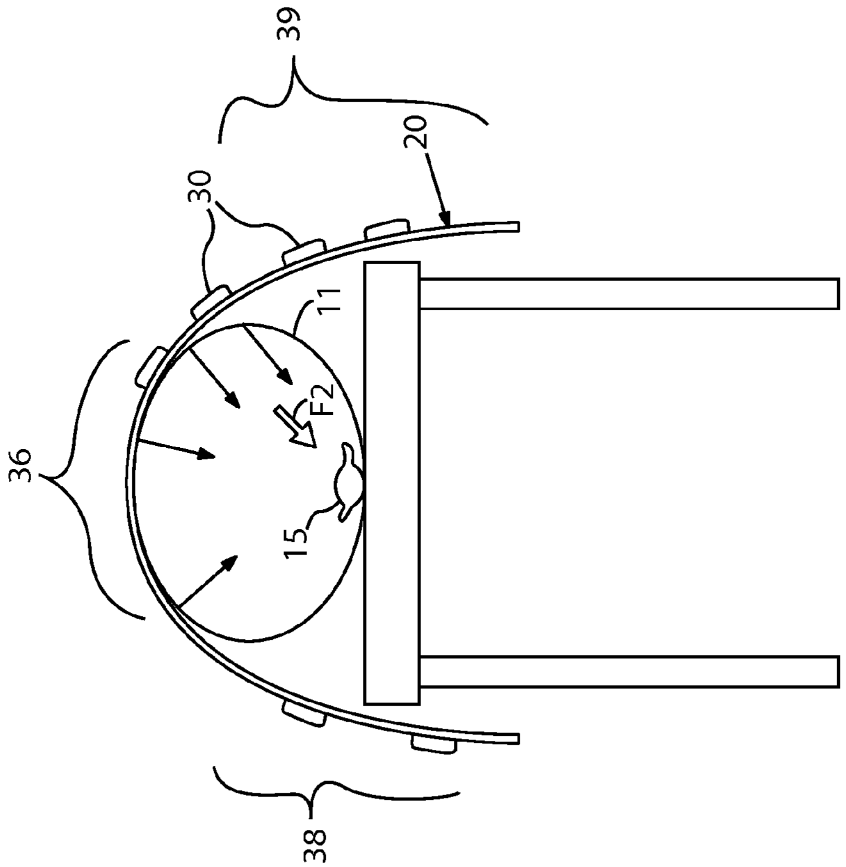
FIG. 3 is the same view as FIG. 2 showing forces from an asymmetrical loading of weight elements.

If a healthcare professional does not want to apply an even downward force to the spine 11, the pressure blanket 20 can be asymmetrically loaded with the weight elements 30. Referring to FIG. 3, it can be seen that more weight elements 30 can be added to one side of the pressure blanket 20 than the other. The weight elements 30 can be added to the hanging straight sections 38, 39 of the pressure blanket 20, and/or the curved section 36 that contacts the patient 11.

If more weight elements 30 are on one side of the pressure blanket 20 than the other, the result is an uneven force being applied to the spine 15. The resultant forces from the weight elements 30 will cause the spine 15 to experience a force F2 that presses the spine 15 away from the more heavily weighted side of the pressure blanket 20. Fine manipulations in the direction and degree of the force affecting the spine can be made by making fine adjustments in the number, size and positions of the weight elements 30 that are added to the pressure blanket 20.

Figure 4:
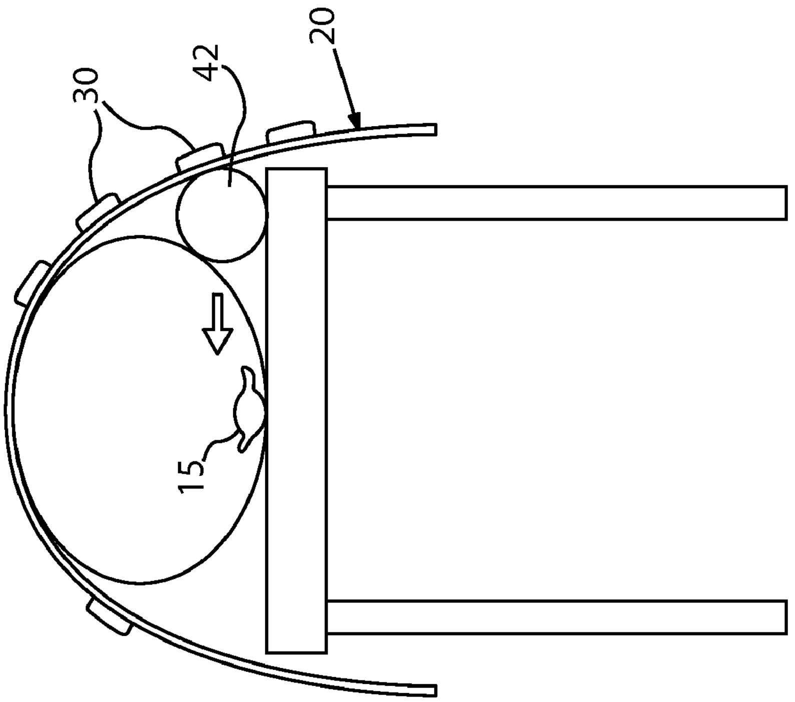
FIG. 4 is the same view as FIG. 2 showing the effect of an additional insert used under the flexible pressure blanket.

Since the pressure blanket 20 hangs over the patient's body, most of the forces applied by the weight elements 30 are experienced as downward forces. If a healthcare provider wants to apply more lateral forces to the spine 15, a secondary object can be placed under the pressure blanket 20. Referring to FIG. 4, a semi-flexible insert 42 is shown being placed next to a patient's body under the pressure blanket 20. The insert 42 is large enough to alter the manner in which the pressure blanket 20 hangs from the body. The result is that the pressure blanket 20 presses against the insert 42. The insert 42, in turn, presses against the body, therein applying a greater lateral force to the spine 15.

In the embodiment of FIGS. 1-4 the patient's body is shown laying upon its back. The weight elements 30 attached to the pressure blanket, therefore, provide a generally downward force to the spine 15 in opposition to the lordotic curvature of the spine 15. It will be understood that if a healthcare provider determines that the spine 15 should be manipulated in a different manner, the same pressure blanket 20 can be used upon a patient lying upon his/her stomach or side. However, since the spine 15 will no longer be at the center bottom of the torso, forces from the pressure blanket 20 will not concentrate at the spine 15. However, for some patients, this may be a desired manipulation.

It will be understood that the embodiment of the present invention system that is illustrated and described is only exemplary. A person skilled in the art can make many variations and alternate embodiments. For instance, the width and length of the pressure blanket can be altered. Furthermore, the shape, size and means of attachment for the weight elements can be altered. All such variations, modifications and alternate embodiments are intended to be included within the scope of the present invention as defined by the claims.

What is claimed is:

1. A method of applying therapeutic forces to the vertebrae contained within a section of a patient's spine, said method comprising the steps of:

providing a flexible pressure blanket having a top surface and a bottom surface that extend between two opposite ends;

having a patient lay in a supine position on an elevated platform;

draping said flexible pressure blanket over said patient, wherein a central section of said flexible pressure blanket contacts the patient and end sections of said pressure blanket, proximate said two opposite ends of said flexible pressure blanket, dangle freely on opposite sides of said patient; and attaching removable weight elements to said pressure blanket in said central section to effect therapeutic forces upon the spine of the patient.

2. The method according to claim 1, wherein said step of providing a flexible pressure blanket further includes providing a flexible pressure blanket with a indicia at a midway between said two opposite ends, wherein said indicia indicate average spacing between spine vertebrae.

3. The method according to claim 2, wherein said step of draping said flexible pressure blanket over said patient includes positioning said flexible pressure blanket so that said indicia are aligned over the spine of the patient.

4. The method according to claim 2, wherein said step of attaching removable weight elements includes attaching said removable weight elements to said flexible pressure blanket in line with at least some of said indicia.

5. The method according to claim 1, wherein said step of attaching removable weight elements includes attaching said removable weight elements to said flexible pressure blanket symmetrically on either side of the patient.

6. The method according to claim 1, wherein said step of attaching removable weight elements includes attaching said removable weight elements to said flexible pressure blanket asymmetrically on either side of the patient.

7. The method according to claim 1, wherein said step of attaching removable weight elements includes attaching said removable weight elements to said flexible pressure blanket in said end sections.

8. The method according to claim 1, further including the step of providing an insert and placing said insert under said flexible pressure blanket, wherein said insert transfers forces from said flexible pressure blanket to the patient.

9. An assembly for applying therapeutic forces to the vertebra contained within a section of a patient's spine, said assembly comprising:

a flexible pressure blanket having a top surface and a bottom surface that extends between two opposite ends;

indicia disposed on said top surface of said flexible pressure blanket midway between said two opposite ends, wherein said indicia indicates spine vertebrae spacing;

a plurality of weight elements; and a plurality of attachment points on said top surface where said plurality of weight elements can be selectively attached to said flexible pressure blanket, wherein said plurality of attachment points align with said indicia.

10. The assembly according to claim 9, wherein said flexible pressure blanket has a length of at least thirty-six inches.

11. The assembly according to claim 10, wherein said flexible pressure blanket has a width of between eight inches and twenty-four inches.

12. The assembly according to claim 9, wherein said weight elements selectively attach to said flexible pressure blanket with hook and loop fasteners.

13. A method of applying forces to the vertebrae in the spine of a person lying in a supine position, said method comprising the steps of:

providing a flexible blanket having indicia thereon that provides an indication of average spacing between spine vertebrae;

draping a flexible blanket over the patient so that sections of said blanket dangle from opposite sides of the patient; and selectively attaching weight elements to said sections of said flexible blanket to create a therapeutic force that acts upon the spine of the patient.

14. The method according to claim 13, wherein said step of selectively attaching weight elements includes attaching weight elements to said flexible blanket so that said weight elements are in alignment with individual vertebrae of the spine beneath said flexible blanket.

15. The method according to claim 13, wherein said step of draping said flexible blanket over said patient includes positioning said flexible blanket so that said indicia are aligned over the spine of the patient.

* * * * *